(12) United States Patent
Kojima et al.

(10) Patent No.: US 9,775,832 B2
(45) Date of Patent: Oct. 3, 2017

(54) PHARMACEUTICAL COMPOSITION FOR ORAL ADMINISTRATION

(71) Applicant: ASTELLAS PHARMA INC., Tokyo (JP)

(72) Inventors: Hiroyuki Kojima, Tokyo (JP); Masakazu Miyazaki, Tokyo (JP); Mare Nishiura, Tokyo (JP); Takashi Nishizato, Tokyo (JP)

(73) Assignee: ASTELLAS PHARMA INC., Tokyo (JP)

( * ) Notice: Subject to any disclaimer, the term of this patent is extended or adjusted under 35 U.S.C. 154(b) by 0 days.

(21) Appl. No.: 15/319,355

(22) PCT Filed: Jun. 24, 2015

(86) PCT No.: PCT/JP2015/068139
§ 371 (c)(1),
(2) Date: Dec. 15, 2016

(87) PCT Pub. No.: WO2015/199115
PCT Pub. Date: Dec. 30, 2015

(65) Prior Publication Data
US 2017/0143678 A1 May 25, 2017

(30) Foreign Application Priority Data

Jun. 24, 2014 (JP) .................. 2014-129374

(51) Int. Cl.
*A61K 31/4184* (2006.01)
*A61K 47/38* (2006.01)
*A61K 9/00* (2006.01)
*A61K 9/20* (2006.01)
*A61K 9/28* (2006.01)

(52) U.S. Cl.
CPC ........ *A61K 31/4184* (2013.01); *A61K 9/0053* (2013.01); *A61K 9/2013* (2013.01); *A61K 9/2018* (2013.01); *A61K 9/2054* (2013.01); *A61K 9/2077* (2013.01); *A61K 9/2095* (2013.01); *A61K 9/28* (2013.01); *A61K 47/38* (2013.01)

(58) Field of Classification Search
CPC .............. A61K 31/4184; A61K 9/0053; A61K 9/2013; A61K 9/2018; A61K 9/2054; A61K 9/2095; A61K 9/28; A61K 47/38; A61K 9/2077
USPC ........................................................ 514/394
See application file for complete search history.

(56) References Cited

U.S. PATENT DOCUMENTS

| | | | |
|---|---|---|---|
| 4,343,789 | A | 8/1982 | Kawata et al. |
| 4,404,183 | A | 9/1983 | Kawata et al. |
| 2002/0031547 | A1 | 3/2002 | Takagi et al. |
| 2009/0181964 | A1 | 7/2009 | Hirano et al. |
| 2015/0259299 | A1 | 9/2015 | Kikuchi et al. |

FOREIGN PATENT DOCUMENTS

| | | |
|---|---|---|
| JP | 59-48810 | 11/1984 |
| JP | 2010-143836 A | 7/2010 |
| JP | 2013-180961 A | 9/2013 |
| JP | 2014-51470 A | 3/2014 |
| WO | 98/29137 | 7/1998 |
| WO | 01/47495 | 7/2001 |
| WO | 2006/106812 A1 | 10/2006 |
| WO | 2012/144592 A1 | 10/2012 |
| WO | 2013/130584 A2 | 9/2013 |
| WO | 2014/038663 A1 | 3/2014 |

OTHER PUBLICATIONS

International Search Report; PCT/JP2015/068139 dated Aug. 3, 2015.
International Searching Authority; Written Opinion; PCT/JP2015/068139; dated Aug. 11, 2015.

*Primary Examiner* — Kristin Vajda
(74) *Attorney, Agent, or Firm* — Kilpatrick Townsend & Stockton LLP

(57) ABSTRACT

Provided is a pharmaceutical composition for oral administration enabling improved solubility, improved dissolution properties, and improved oral absorbability of (2R)—N-({5-[3-(2,5-difluorophenyl)-2-(1,3-dihydro-2H-benzimidazole-2-ylidene)-3-oxopropanoyl]-2-fluorophenyl}sulfonyl)-2-hydroxypropane imide amide (hereinafter referred to as compound A) or a pharmaceutically acceptable salt thereof, as well as size reduction. The pharmaceutical composition for oral administration contains an amorphous form of compound A or its pharmaceutically acceptable salt, and a polymer.

17 Claims, 3 Drawing Sheets

PHARMACEUTICAL COMPOSITION FOR ORAL ADMINISTRATION

CROSS-REFERENCE TO RELATED APPLICATIONS

The present application is a §371 National Phase Application of PCT/JP2015/068139, filed Jun. 24, 2015, which application claims priority to JP 2014-129374, filed Jun. 24, 2014, the disclosures of which are hereby incorporated by reference in their entireties for all purposes.

TECHNICAL FIELD

The present invention relates to a pharmaceutical composition for oral administration enabling improved oral absorbability of (2R)—N-({5-[3-(2,5-difluorophenyl)-2-(1,3-dihydro-2H-benzimidazole-2-ylidene)-3-oxopropanoyl]-2-fluorophenyl}sulfonyl)-2-hydroxypropane imide amide or a pharmaceutically acceptable salt thereof, which is a poorly-soluble drug.

More particularly, the present invention relates to a pharmaceutical composition for oral administration, comprising an amorphous form of (2R)—N-({5-[3-(2,5-difluorophenyl)-2-(1,3-dihydro-2H-benzimidazole-2-ylidene)-3-oxopropanoyl]-2-fluorophenyl}sulfonyl)-2-hydroxypropane imide amide or a pharmaceutically acceptable salt thereof, and a polymer.

BACKGROUND ART

It is known that (2R)—N-({5-[3-(2,5-difluorophenyl)-2-(1,3-dihydro-2H-benzimidazole-2-ylidene)-3-oxopropanoyl]-2-fluorophenyl}sulfonyl)-2-hydroxypropane imide amide (hereinafter sometimes referred to as compound A) of the formula:

[Chem. 1]

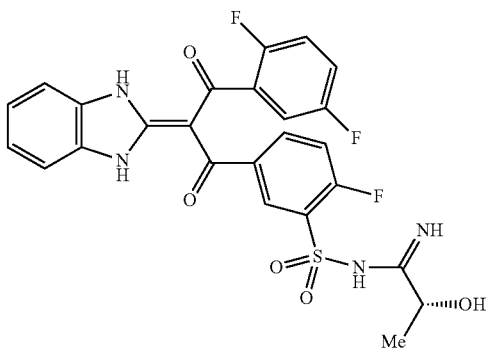

and its optical isomer, (2S)—N-({5-[3-(2,5-difluorophenyl)-2-(1,3-dihydro-2H-benzimidazole-2-ylidene)-3-oxopropanoyl]-2-fluorophenyl}sulfonyl)-2-hydroxypropane imide amide (hereinafter sometimes referred to as compound B), have an antagonistic activity against a gonadotropin releasing hormone (GnRH) receptor, and are useful as active ingredients of a therapeutic agent for sex hormone-dependent diseases, such as prostate cancer, benign prostatic hyperplasia, breast cancer, endometriosis, and/or uterine fibroid (Patent Literature 1). Further, compound A and a method of manufacturing the same are known (Patent Literatures 2 and 3).

With respect to the compound, in order to effectively express the pharmacological effects of the active ingredient and remit or cure indications of interest, it is necessary to select an appropriate dosage form and formulation depending on, needless to say, the pharmacological properties of the active ingredient, as well as its physicochemical properties, the type and disease state of indications of interest, and the like.

However, although a compound selected on the basis of excellent pharmacological effects is expected to exhibit fast-acting properties against its indications, it is often found to be poorly soluble. Since a poorly soluble drug also exhibits low solubility in the digestive tract, the problem is not only that the absorbability from the mucous membrane of the digestive tract is low, but also that the fast-acting properties are not expected.

Therefore, even in the current situation, formulation design to improve the solubility and the oral absorbability of a poorly soluble drug is an important technical problem for the efficacy expression of the poorly soluble drug.

Conventionally, as methods of improving the solubility and oral absorbability of a poorly soluble drug, a method in which a drug is refined, a method in which a solid dispersion is formed, or the like, are known. Among these methods, it is considered that the method in which a solid dispersion is formed is a practically versatile method to improve the solubility and oral absorbability of poorly soluble drugs (Patent Literatures 4 and 5).

Further, as a technique for improving the solubility of a poorly soluble drug, an invention in which a polymer is added to a poorly soluble drug, which can be present in either a crystalline form or an amorphous form, so that the maximum concentration of the drug becomes at least 1.25 times, is known (Patent Literature 6).

However, as compound A or a pharmaceutically acceptable salt thereof, in which the dose is 100 mg or more depending on indications, since it is necessary, when it is formulated, to take into consideration not only the improvement of solubility and oral absorbability, but also downsizing (compactification), there is room for further improvement with respect to the solubilization technique of poorly soluble drugs.

CITATION LIST

Patent Literature

[Patent Literature 1] WO 2006/106812
[Patent Literature 2] WO 2014/038663
[Patent Literature 3] Japanese Unexamined Patent Publication (Kokai) No. 2014-51470
[Patent Literature 4] Japanese Examined Patent Publication (Kokoku) No. 59-48810
[Patent Literature 5] WO 98/29137
[Patent Literature 6] WO 01/047495

SUMMARY OF INVENTION

Technical Problem

An object of the present invention is to provide a pharmaceutical composition for oral administration enabling improved solubility, improved dissolution properties, and improved oral absorbability of compound A or a pharmaceutically acceptable salt thereof, as well as size reduction.

Solution to Problem

The solubility in an acidic pH range (first fluid for dissolution test of the Japanese Pharmacopoeia (JP1 (pH 1.2))) of compound A in the crystalline state is about 0.0099 mg/mL, and the solubility in a neutral pH range (second fluid for dissolution test of the Japanese Pharmacopoeia (JP2 (pH 6.8))) thereof is about 0.0098 mg/mL. Compound A exhibits low solubility in both the acidic pH range and the neutral pH range.

Under these circumstances, the inventors focused on the improvement of the solubility of compound A, and conducted studies to confirm the following, and completed the present invention. A solid dispersion consisting of compound A and a polymer (Example 1) generated a few degradation products, and was stable (Experimental Example 4), and improved the solubility and the oral absorbability (Experimental Examples 1, 2, and 6). An amorphous form of compound A (Example 2) alone improved the solubility, in the state that a polymer having a function to maintain an amorphous form, as a solid dispersion, was not presented (Experimental Example 3), and did not convert into a crystalline form under various storage conditions (Experimental Example 5), and generated a few degradation products, and was stable (Experimental Example 4), and improved the oral absorbability (Experimental Example 6). Tablets containing the amorphous form and polymers (Examples 3 to 8 and 15 to 18) did not convert into a crystalline form under various storage conditions (Experimental Example 8), and improved the solubility (Experimental Examples 8, 9, and 11), and maintained a supersaturated state for a long period of time (Experimental Example 10), and exhibited good stability (Experimental Examples 8 and 9) and disintegration properties (Experimental Example 7).

The present invention relates to:

[1] a pharmaceutical composition for oral administration, comprising an amorphous form of (2R)—N-({5-[3-(2,5-difluorophenyl)-2-(1,3-dihydro-2H-benzimidazole-2-ylidene)-3-oxopropanoyl]-2-fluorophenyl}sulfonyl)-2-hydroxypropane imide amide or a pharmaceutically acceptable salt thereof, and a polymer,

[2] the pharmaceutical composition for oral administration of [1], wherein the polymer is a polymer or two or more polymers selected from the group consisting of hypromellose, hydroxypropyl methylcellulose acetate succinate, polyvinyl pyrrolidone, hydroxypropyl cellulose, polyethylene glycol, copolyvidone, and polyvinyl alcohol,

[3] the pharmaceutical composition for oral administration of [1] or [2], wherein the mixing ratio of the polymer is about 10% by weight to about 500% by weight with respect to the weight of the amorphous form of (2R)—N-({5-[3-(2,5-difluorophenyl)-2-(1,3-dihydro-2H-benzimidazole-2-ylidene)-3-oxopropanoyl]-2-fluorophenyl}sulfonyl)-2-hydroxypropane imide amide or a pharmaceutically acceptable salt thereof,

[4] the pharmaceutical composition for oral administration of any one of [1] to [3], wherein the mixing ratio of the polymer is about 0.01% by weight to about 30% by weight with respect to the total weight of the pharmaceutical composition for oral administration,

[5] the pharmaceutical composition for oral administration of any one of [1] to [4], wherein the polymer is hypromellose and/or polyethylene glycol,

[6] the pharmaceutical composition for oral administration of any one of [1] to [5], wherein the polymer is hypromellose,

[7] the pharmaceutical composition for oral administration of any one of [1] to [6], wherein the polymer is contained as a binder and/or a base material for film coating,

[8] the pharmaceutical composition for oral administration of any one of [1] to [7], wherein the pharmaceutical composition for oral administration is a tablet,

[9] the pharmaceutical composition for oral administration of any one of [1] to [8], further comprising a disintegrating agent,

[10] the pharmaceutical composition for oral administration of [9], wherein the disintegrating agent is croscarmellose sodium,

[11] the pharmaceutical composition for oral administration of [9] or [10], wherein the mixing ratio of the disintegrating agent is about 0.1% by weight to about 30% by weight with respect to the total weight of the pharmaceutical composition,

[12] a stable pharmaceutical composition for oral administration, comprising an amorphous form of (2R)—N-({5-[3-(2,5-difluorophenyl)-2-(1,3-dihydro-2H-benzimidazole-2-ylidene)-3-oxopropanoyl]-2-fluorophenyl}sulfonyl)-2-hydroxypropane imide amide or a pharmaceutically acceptable salt thereof,

[13] the pharmaceutical composition for oral administration of [12], further comprising a pharmaceutical additive,

[14] a process of manufacturing a pharmaceutical composition for oral administration comprising an amorphous form of (2R)—N-({5-[3-(2,5-difluorophenyl)-2-(1,3-dihydro-2H-benzimidazole-2-ylidene)-3-oxopropanoyl]-2-fluorophenyl}sulfonyl)-2-hydroxypropane imide amide or a pharmaceutically acceptable salt thereof, and a polymer,

[15] a pharmaceutical composition for oral administration, prepared by spray drying, and comprising an amorphous form of (2R)—N-({5-[3-(2,5-difluorophenyl)-2-(1,3-dihydro-2H-benzimidazole-2-ylidene)-3-oxopropanoyl]-2-fluorophenyl}sulfonyl)-2-hydroxypropane imide amide or a pharmaceutically acceptable salt thereof, and a polymer,

[16] a pharmaceutical composition for oral administration, prepared using a solvent containing acetone, and comprising an amorphous form of (2R)—N-({5-[3-(2,5-difluorophenyl)-2-(1,3-dihydro-2H-benzimidazole-2-ylidene)-3-oxopropanoyl]-2-fluorophenyl}sulfonyl)-2-hydroxypropane imide amide or a pharmaceutically acceptable salt thereof, and a polymer,

[17] a stable pharmaceutical composition for oral administration, prepared by spray drying, comprising an amorphous form of (2R)—N-({5-[3-(2,5-difluorophenyl)-2-(1,3-dihydro-2H-benzimidazole-2-ylidene)-3-oxopropanoyl]-2-fluorophenyl}sulfonyl)-2-hydroxypropane imide amide or a pharmaceutically acceptable salt thereof,

[18] a stable pharmaceutical composition for oral administration, prepared using a solvent containing acetone, comprising an amorphous form of (2R)—N-({5-[3-(2,5-difluorophenyl)-2-(1,3-dihydro-2H-benzimidazole-2-ylidene)-3-oxopropanoyl]-2-fluorophenyl}sulfonyl)-2-hydroxypropane imide amide or a pharmaceutically acceptable salt thereof,

[19] a pharmaceutical composition for oral administration, comprising an amorphous form of (2S)—N-({5-[3-(2,5-difluorophenyl)-2-(1,3-dihydro-2H-benzimidazole-2-ylidene)-3-oxopropanoyl]-2-fluorophenyl}sulfonyl)-2-hydroxypropane imide amide or a pharmaceutically acceptable salt thereof, and a polymer,

[20] a process of manufacturing a pharmaceutical composition for oral administration, comprising:
(1) preparing an amorphous form of (2R)—N-({5-[3-(2,5-difluorophenyl)-2-(1,3-dihydro-2H-benzimidazole-2-ylidene)-3-oxopropanoyl]-2-fluorophenyl}sulfonyl)-2-hydroxypropane imide amide or a pharmaceutically acceptable salt thereof by spray drying, and
(2) adding a polymer to the amorphous form of (1),
[21] a process of manufacturing a pharmaceutical composition for oral administration, comprising:
(1) preparing an amorphous form of (2R)—N-({5-[3-(2,5-difluorophenyl)-2-(1,3-dihydro-2H-benzimidazole-2-ylidene)-3-oxopropanoyl]-2-fluorophenyl}sulfonyl)-2-hydroxypropane imide amide or a pharmaceutically acceptable salt thereof, using a solvent containing acetone, and
(2) adding a polymer to the amorphous form of (1),
[22] a process of manufacturing a stable pharmaceutical composition for oral administration, comprising the step of preparing an amorphous form of (2R)—N-({5-[3-(2,5-difluorophenyl)-2-(1,3-dihydro-2H-benzimidazole-2-ylidene)-3-oxopropanoyl]-2-fluorophenyl}sulfonyl)-2-hydroxypropane imide amide or a pharmaceutically acceptable salt thereof by spray drying,
[23] a process of manufacturing a stable pharmaceutical composition for oral administration, comprising the step of preparing an amorphous form of (2R)—N-({5-[3-(2,5-difluorophenyl)-2-(1,3-dihydro-2H-benzimidazole-2-ylidene)-3-oxopropanoyl]-2-fluorophenyl}sulfonyl)-2-hydroxypropane imide amide or a pharmaceutically acceptable salt thereof, using a solvent containing acetone,
[24] a process of manufacturing a pharmaceutical composition for oral administration, comprising:
(1) preparing an amorphous form of (2S)—N-({5-[3-(2,5-difluorophenyl)-2-(1,3-dihydro-2H-benzimidazole-2-ylidene)-3-oxopropanoyl]-2-fluorophenyl}sulfonyl)-2-hydroxypropane imide amide or a pharmaceutically acceptable salt thereof, and
(2) adding a polymer to the amorphous form of (1), and
[25] a process of manufacturing a stable pharmaceutical composition for oral administration, comprising:
(1) dissolving (2R)—N-({5-[3-(2,5-difluorophenyl)-2-(1,3-dihydro-2H-benzimidazole-2-ylidene)-3-oxopropanoyl]-2-fluorophenyl}sulfonyl)-2-hydroxypropane imide amide or a pharmaceutically acceptable salt thereof in a solvent containing acetone to prepare a solution, and
(2) spray-drying the solution of (1) to prepare an amorphous form of (2R)—N-({5-[3-(2,5-difluorophenyl)-2-(1,3-dihydro-2H-benzimidazole-2-ylidene)-3-oxopropanoyl]-2-fluorophenyl}sulfonyl)-2-hydroxypropane imide amide or a pharmaceutically acceptable salt thereof.

Advantageous Effects of Invention

According to the present invention, a pharmaceutical composition for oral administration enabling improved solubility, improved dissolution properties, and improved oral absorbability of compound A or a pharmaceutically acceptable salt thereof, as well as size reduction, can be provided.

DESCRIPTION OF EMBODIMENTS

Figure 1:
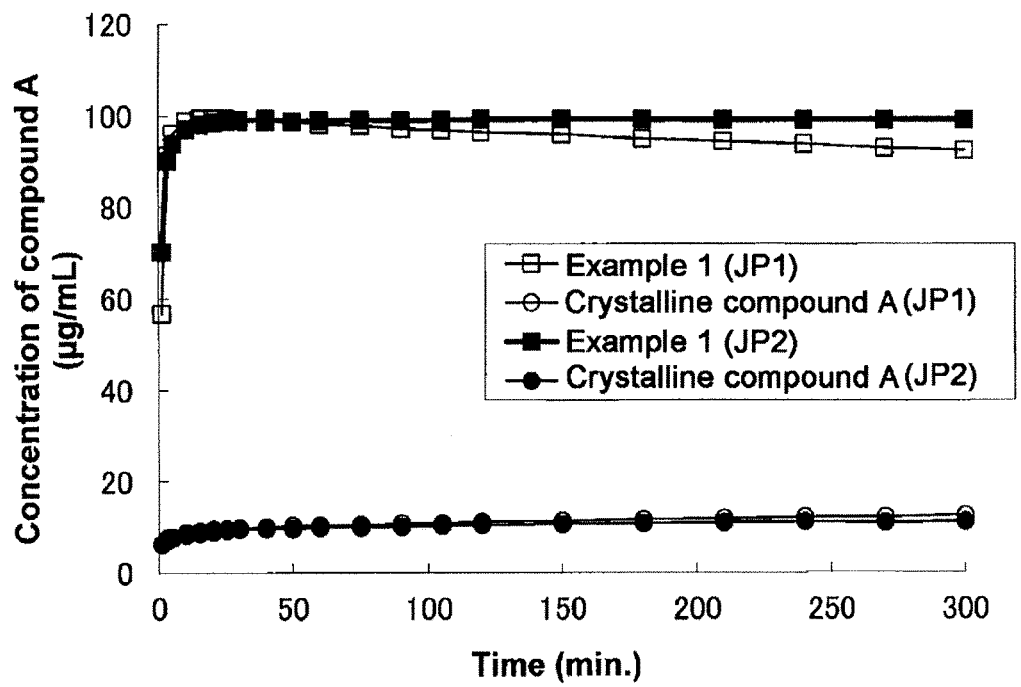
FIG. 1 is a graph showing the results of a dissolution test for compound A in the crystalline state and the solid dispersion of Example 1.

The term "to improve solubility" or "to improve dissolution properties" as used herein means that the solubility or the dissolution rate of compound A or a pharmaceutically acceptable salt thereof in water, a buffer, or the like, is increased. More particularly, for example, when a pharmaceutical composition containing compound A or a pharmaceutically acceptable salt thereof (such as an amorphous form, a solid dispersion, a tablet containing a solid dispersion, or the like) is evaluated by a dissolution test, it is defined in that the solubility or the dissolution rate of compound A or a pharmaceutically acceptable salt thereof in the pharmaceutical composition is 3 or more times higher than that of compound A or a pharmaceutically acceptable salt thereof in the crystalline state.

The term "to improve oral absorbability" as used herein means to have oral absorbability superior to that of a pharmaceutical composition comprising compound A or a pharmaceutically acceptable salt thereof in the crystalline state, in a test subject, such as a dog, a human, or the like. More particularly, for example, when a pharmaceutical composition containing compound A or a pharmaceutically acceptable salt thereof (such as an amorphous form, a solid dispersion, a tablet containing a solid dispersion, or the like) is administered to the test subject, it is defined in that the ratio of Cmax and/or AUC is, for example, 10 or more times, or 50 or more times in an embodiment, higher than that that of a pharmaceutical composition containing compound A or a pharmaceutically acceptable salt thereof in the crystalline state.

The term "stable" as used herein means to have stability against, for example, heat, light, temperature, and/or humidity. For example, after a pharmaceutical composition is allowed to stand under predetermined conditions, it is defined as an embodiment in which the increased amount in percentage of a maximum related substance of compound A contained in the pharmaceutical composition, or the increased amount in the percentage of the total amount of related substances of compound A, is a specific amount or less.

For example, the term "stable" means that the increased amount in percentage of a maximum related substance of compound A after storage at 70° C. for 9 days (sealed) is 0.5% or less in an embodiment, 0.3% or less in an embodiment, and 0.1% or less in an embodiment.

It means that the increased amount in percentage of a maximum related substance of compound A, after storage at 25° C. and 60% relative humidity (hereinafter sometimes referred to as 25° C., 60% RH) for 1 month, at 25° C., 60% RH for 3 months, at 25° C., 60% RH for 6 months, at 40° C. and 75% relative humidity (hereinafter sometimes referred to as 40° C., 75% RH) for 1 month, at 40° C., 75%

RH for 3 months, or at 40° C., 75% RH for 6 months, is 0.5% or less in an embodiment, 0.3% or less in an embodiment, and 0.1% or less in an embodiment.

Further, for example, it means that the increased amount in the percentage of the total amount of related substances of compound A after storage at 70° C. for 9 days (sealed) is 1.0% or less in an embodiment, 0.5% or less in an embodiment, and 0.3% or less in an embodiment.

It means that the increased amount in the percentage of the total amount of related substances of compound A, after storage at 25° C., 60% RH for 1 month, at 25° C., 60% RH for 3 months, at 25° C., 60% RH for 6 months, at 40° C., 75% RH for 1 month, at 40° C., 75% RH for 3 months, or at 40° C., 75% RH for 6 months, is 1.0% or less in an embodiment.

The term "maximum related substance" as used herein means an related substance having the largest peak area among related substances of compound A. More particularly, for example, when the amount of each related substance contained in a pharmaceutical composition is measured by a high-performance liquid chromatographic method (hereinafter referred to as an HPLC method), it is defined in that an related substance having the largest peak area among the obtained related substances is the maximum related substance.

The term "the amount of the maximum related substance" as used herein is defined as the percentage of the maximum related substance with respect to the total peak area of compound A and its related substances, when the peak area of the maximum related substance contained in a pharmaceutical composition is measured by an HPLC method.

The term "the total amount of related substances" as used herein is defined as the sum of the percentage of each related substance of compound A.

The term "an increased amount" in "the maximum related substance" as used herein is defined as the difference between the percentages of the maximum related substance after storage and at the beginning of the storage. The term "an increased amount" in "the total amount of related substances" is defined as the difference between the percentages of the total amount of related substances after storage and at the beginning of the storage.

As an embodiment, the term "stable in the state of an amorphous form alone" as used herein is specifically defined in that compound A or a pharmaceutically acceptable salt thereof is an amorphous form after storage at 70° C. for 9 days (sealed), at 20° C., 60% RH for 1 month, at 20° C., 60% RH for 3 months, at 20° C., 60% RH for 6 months, at 40° C., 75% RH for 1 month, at 40° C., 75% RH for 3 months, or at 40° C., 75% RH for 6 months.

Whether or not compound A or a pharmaceutically acceptable salt thereof is an amorphous form can be confirmed by the fact that a crystalline form is not observed by a powder X-ray diffraction method, the fact that an endothermic peak specific for a crystalline form of compound A or a pharmaceutically acceptable salt thereof is not observed by a thermal analysis, or the like.

Compound A or a pharmaceutically acceptable salt thereof in the crystalline state, which can be used as a material for the active ingredient of the pharmaceutical composition for oral administration of the present invention, can be synthesized by, for example, a method described in Patent Literature 2, a method obvious to those skilled in the art, or a variation thereof.

The term "about" as used herein means, when it is used in connection with numerical variables, a larger variable value, in general, within an experimental error (for example, within the 95% confidence interval for the mean), or within ±10% of the indicated value, and all the values of the variable.

Compound A or a pharmaceutically acceptable salt thereof in the crystalline state can be amorphized by the amorphization step as described below, or the like.

The amorphous form of compound A or a pharmaceutically acceptable salt thereof can be contained in the pharmaceutical composition for oral administration of the present invention, in an arbitrary embodiment, to the extent that the desired effects of the present invention can be achieved. More particularly, for example, the amorphous form of compound A or a pharmaceutically acceptable salt thereof alone can be contained in the pharmaceutical composition for oral administration; a solid dispersion thereof with a polymer can be contained in the pharmaceutical composition for oral administration; or compound A or a pharmaceutically acceptable salt thereof and a polymer (in the state that a solid dispersion is not formed) can be contained in the pharmaceutical composition for oral administration.

Compound A or a pharmaceutically acceptable salt thereof has a potent antagonistic activity against a GnRH receptor, and therefore, is useful as an active ingredient of a therapeutic agent for sex hormone-dependent diseases, in particular, diseases in which GnRH is involved, such as prostate cancer, benign prostatic hyperplasia, breast cancer, endometriosis, uterine fibroid, or the like.

Compound B or a pharmaceutically acceptable salt thereof has an antagonistic activity against a GnRH receptor. Compound B or a pharmaceutically acceptable salt thereof is an optical isomer of compound A or a pharmaceutically acceptable salt thereof, and therefore, the physicochemical properties are basically the same as those of compound A.

The dose of compound A or a pharmaceutically acceptable salt thereof can be appropriately determined depending on the individual case taking into consideration, for example, symptoms of the disease, age of the patient, race, sex, or the like.

The daily dose is, for example, about 0.001 mg/kg to 100 mg/kg, 0.1 mg/kg to 30 mg/kg in an embodiment, and 0.1 mg/kg to 10 mg/kg in an embodiment, which is administered once or divided into two to four doses per day.

The content of the amorphous form of compound A or a pharmaceutically acceptable salt thereof is, for example, about 0.001 mg to about 1000 mg, about 0.01 mg to about 150 mg in an embodiment, and about 0.1 mg to about 150 mg in an embodiment, with respect to the pharmaceutical composition for oral administration. In an embodiment, it is about 1 mg, about 5 mg, about 7.5 mg, about 10 mg, and about 100 mg.

The content ratio of the amorphous form of compound A or a pharmaceutically acceptable salt thereof is, for example, about 0.001% by weight to about 99% by weight, about 0.1% by weight to about 50% by weight in an embodiment, and about 0.1% by weight to about 30% by weight in an embodiment, with respect to the total weight of the pharmaceutical composition for oral administration.

The polymer used in the present invention is not particularly limited, so long as it is pharmaceutically acceptable.

More particularly, examples of the polymer include hypromellose, hydroxypropyl methylcellulose acetate succinate, polyvinyl pyrrolidone, hydroxypropyl cellulose, polyethylene glycol, copolyvidone, polyvinyl alcohol, methyl cellulose, ethyl cellulose, polyvinyl alcohol/polyethylene glycol graft copolymer, hydroxyethyl cellulose, methyl hydroxyethyl cellulose, carboxymethyl cellulose, carboxymethyl ethyl cellulose, hydroxypropyl methylcellulose phthalate, aminoalkyl methacrylate copolymer E, methacrylic acid copolymer L, dry methacrylic acid copolymer LD, methacrylic acid copolymer LD, methacrylic acid copolymer S, aminoalkyl methacrylate copolymer RS, and the like. In an embodiment, the examples thereof include hypromellose, hydroxypropyl methylcellulose acetate succinate, and polyethylene glycol; in an embodiment, the examples thereof include hypromellose and polyethylene glycol; and in an embodiment, the examples thereof include hypromellose.

Examples of hypromellose include product names TC-5E (viscosity: 3 mPa·s, 2% W/V aqueous solution at 20° C., Shin-Etsu Chemical Co., Ltd.), TC-5R (viscosity: 6 mPa·s, 2% W/V aqueous solution at 20° C., Shin-Etsu Chemical Co., Ltd.), TC-5S (viscosity: 15 mPa·s, 2% W/V aqueous solution at 20° C., Shin-Etsu Chemical Co., Ltd.), and the like.

Examples of hydroxypropyl methylcellulose acetate succinate include product names AQOAT LG grade (Shin-Etsu Chemical Co., Ltd.), AQOAT MG grade (Shin-Etsu Chemical Co., Ltd.), AQOAT HG grade (Shin-Etsu Chemical Co., Ltd.), and the like.

Examples of polyvinyl pyrrolidone include product name PVP K30 (BASF), and the like.

Examples of hydroxypropyl cellulose include product names HPC-SSL (viscosity: 3.0 to 5.9 mPa·s, 2% W/V aqueous solution at 20° C., Nippon Soda Co., Ltd.), HPC-SL (viscosity: 2.0 to 2.9 mPa·s, 2% W/V aqueous solution at 20° C., Nippon Soda Co., Ltd.), HPC-L (viscosity: 6.0 to 10.0 mPa·s, 2% W/V aqueous solution at 20° C., Nippon Soda Co., Ltd.), and the like.

Examples of polyethylene glycol include product name Polyglykol 8000PF (Clariant), and the like.

Examples of copolyvidone include product names Kollidon VA64 (BASF), Kollidon VA64 Fine (BASF), and the like.

Examples of polyvinyl alcohol include product names GOHSENOL EG-40 (The Nippon Synthetic Chemical Industry Co., Ltd.), GOHSENOL EG-40P (The Nippon Synthetic Chemical Industry Co., Ltd.), GOHSENOL EG-05 (The Nippon Synthetic Chemical Industry Co., Ltd.), GOHSENOL EG-05P (The Nippon Synthetic Chemical Industry Co., Ltd.), and the like.

The polymer can be added to the pharmaceutical composition for oral administration of the present invention by an arbitrary method, to the extent that the desired effects of the present invention can be achieved. More particularly, for example, the amorphous form of compound A or a pharmaceutically acceptable salt thereof may form a solid dispersion with the polymer; the amorphous form of compound A or a pharmaceutically acceptable salt thereof may be simply mixed with the polymer; the amorphous form of compound A or a pharmaceutically acceptable salt thereof may be granulated with the polymer; or the polymer may be further added (for example, as a film-coating base material) to a granulated product, a mixed product before tableting, or a compression-molded product, each of which contains the amorphous form of compound A or a pharmaceutically acceptable salt thereof.

As an embodiment, an embodiment in which the amorphous form of compound A or a pharmaceutically acceptable salt thereof is granulated with the polymer; or an embodiment in which the polymer is further added to a granulated product, a mixed product before tableting, or a compression-molded product, each of which contains the amorphous form of compound A or a pharmaceutically acceptable salt thereof; may be exemplified.

The polymer can be added as, for example, a carrier for a solid dispersion, a binder, and/or a film-coating base material for a film coating layer. In an embodiment, it can be added as a binder and/or a film-coating base material for a film coating layer.

The polymer can be appropriately added alone, or as a combination of two or more, in appropriate amounts.

The content of the polymer is not particularly limited, so long as the solubility, dissolution properties, and/or oral absorbability of compound A or its pharmaceutically acceptable salt thereof are improved. The content ratio of the polymer is, for example, about 0.01% by weight to about 60% by weight, and about 0.01% by weight to 30% by weight in an embodiment, with respect to the total weight of the pharmaceutical composition for oral administration.

In the case where the amorphous form of compound A or its pharmaceutically acceptable salt thereof and the polymer form a solid dispersion, the content ratio of the polymer is, for example, about 10% by weight to about 500% by weight, about 10% by weight to about 300% by weight in an embodiment, and about 50% by weight to about 200% by weight in an embodiment, with respect to the amorphous form of compound A or its pharmaceutically acceptable salt thereof.

In the case where the amorphous form of compound A or its pharmaceutically acceptable salt thereof and the polymer are simply mixed; in the case where the amorphous form of compound A or its pharmaceutically acceptable salt thereof and the polymer are granulated; or in the case where the polymer is further added to a granulated product, a mixed product before tableting, or a compression-molded product, each of which contains the amorphous form of compound A or a pharmaceutically acceptable salt thereof; the content ratio of the polymer is, for example, about 0.01% by weight to about 30% by weight, about 0.1% by weight to about 20% by weight in an embodiment, about 1% by weight to about 15% by weight in an embodiment, and about 1% by weight to about 10% by weight in an embodiment, with respect to the total weight of the pharmaceutical composition for oral administration.

The disintegrating agent used in the present invention is not particularly limited, so long as it imparts a function that achieves rapid dissolution properties of compound A or a pharmaceutically acceptable salt thereof, to the formulation.

More particularly, examples of the disintegrating agent include croscarmellose sodium, low-substituted hydroxypropyl cellulose, crospovidone, sodium starch glycolate, carmellose calcium, carmellose sodium, and the like. In an embodiment, it is croscarmellose sodium.

Examples of croscarmellose sodium include the product names Kiccolate ND-200 (Asahi Kasei Chemicals Corporation), Kiccolate ND-2HS (Asahi Kasei Chemicals Corporation), Ac-Di-Sol (FMC), and the like.

Examples of low-substituted hydroxypropyl cellulose include the product names L-HPC LH11 (Shin-Etsu Chemical Co., Ltd.), L-HPC LH21 (Shin-Etsu Chemical Co., Ltd.), L-HPC LH22 (Shin-Etsu Chemical Co., Ltd.), L-HPC LH31 (Shin-Etsu Chemical Co., Ltd.), L-HPC LH32 (Shin-Etsu Chemical Co., Ltd.), and the like.

Examples of crospovidone include the product name Kollidon CL(BASF), and the like.

Examples of sodium starch glycolate include the product name Primojel (DFE pharma), and the like.

Examples of carmellose calcium include the product name ECG-505 (GOTOKU CHEMICAL CO., LTD.), and the like.

Examples of carmellose sodium include the product name CMC DICEL (Daicel Chemical Industries Ltd.), and the like.

The disintegrating agent can be appropriately added alone, or as a combination of two or more, in appropriate amounts.

The content of the disintegrating agent is not particularly limited, so long as it can achieve rapid dissolution properties of compound A or a pharmaceutically acceptable salt thereof. The content ratio of the disintegrating agent is, for example, about 0.1% by weight to about 30% by weight, about 0.5% by weight to about 20% by weight in an embodiment, about 1% by weight to about 10 by weight in an embodiment, about 2% by weight to about 10 by weight in an embodiment, about 4% by weight to about 10 by weight in an embodiment, with respect to the total weight of the pharmaceutical composition for oral administration.

The pharmaceutical composition for oral administration of the present invention may be, for example, tablets, capsules, granules, powder, fine granules, or the like, and tablets in an embodiment.

In the pharmaceutical composition for oral administration of the present invention, it may be formulated by appropriately using various pharmaceutical additives, if desired, to the extent that the desired effects of the present invention can be achieved. Such pharmaceutical additives are not particularly limited, so long as they are pharmaceutically acceptable and pharmacologically acceptable. Examples of the pharmaceutical additives include fillers, corrigents, effervescent agents, sweeteners, flavors, lubricants, buffers, antioxidants, surfactants, glidants, and the like.

Examples of the fillers include lactose, sucrose, D-mannitol, D-sorbitol, starch, gelatinized starch, dextrin, crystalline cellulose, low substituted hydroxypropylcellulose, carboxymethylcellulose sodium, gum arabic, pullulan, light anhydrous silicic acid, synthetic aluminum silicate, magnesium aluminate metasilicate, and the like.

Examples of the corrigents include citric acid, tartaric acid, malic acid, and the like.

Examples of the effervescent agents include sodium bicarbonate, and the like.

Examples of the sweeteners include saccharin sodium, dipotassium glycyrrhizinate, aspartame, stevia, thaumatin, and the like.

Examples of the flavors include lemon, lemon-lime, orange, menthol, and the like.

Examples of the lubricants include magnesium stearate, calcium stearate, and the like.

Examples of the buffers include citric acid, succinic acid, fumaric acid, tartaric acid, ascorbic acid, and salts thereof; glutamic acid, glutamine, glycine, aspartic acid, alanine, arginine, and salts thereof; magnesium oxide, zinc oxide, magnesium hydroxide, phosphoric acid, boric acid, and salts thereof; and the like.

Examples of the antioxidants include ascorbic acid, dibutyl hydroxytoluene, propyl gallate, and the like.

Examples of the surfactants include polysorbate 80, sodium lauryl sulfate, polyoxyethylene hydrogenated castor oil, and the like.

Examples of the glidants include light anhydrous silicic acid, and the like.

These pharmaceutical additives may be appropriately added alone, or as a combination of two or more, in appropriate amounts. With respect to the contents of the pharmaceutical additives, each pharmaceutical additive may be contained in an amount such that the desired effects of the present invention may be achieved.

The pharmaceutical composition for oral administration of the present invention can be produced in accordance with known methods including, for example, amorphization of compound A or a pharmaceutically acceptable salt thereof, mixing, granulation, drying, forming (tableting), film coating, and the like.

The process of manufacturing the pharmaceutical composition for oral administration of the present invention will be explained below.

Amorphization Step

A method of amorphizing compound A or a pharmaceutically acceptable salt thereof, or a method of preparing the solid dispersion of compound A or a pharmaceutically acceptable salt thereof with the polymer is not particularly limited, so long as it is a conventional method of amorphizing a drug, or a conventional method of preparing a solid dispersion. Examples of such methods include a solvent method, a melting method, a mechanochemical method, and the like. The solvent method is preferable.

Examples of the solvent method include a method in which after compound A or a pharmaceutically acceptable salt thereof is dissolved or suspended in a solvent, the solvent is removed; a method in which after compound A or a pharmaceutically acceptable salt thereof and the polymer are dissolved or suspended in a solvent, the solvent is removed; and the like.

The solvent is not particularly limited, so long as compound A or a pharmaceutically acceptable salt thereof (and the polymer, if any) can be dissolved or suspended in the solvent. Examples of the solvent include methanol, dichloromethane, water, ethanol, acetone, propylene glycol, dimethyl sulfoxide, and the like; the examples include methanol and water in an embodiment; and the examples include acetone and water in an embodiment. Preferred examples include methanol and water. These solvents can be appropriately used alone, or as a combination of two or more, in appropriate amounts. As an embodiment, it is a mixed solvent of methanol with dichloromethane, a mixed solvent of methanol with water, or a mixed solvent of acetone with water, and among these, the mixed solvent of acetone with water is preferable. The content of water in the pharmaceutically acceptable solvent is preferably from more than 0% by weight to less than 50% by weight. The ratio (acetone: water) is, for example, 9.9:0.1 to 0.1:9.9, 9.9:0.1 to 5.0:5.0 in an embodiment, and 9.5:0.5 to 8.5:1.5 in an embodiment.

Examples of a method of removing the solvent include spray drying, freeze drying, and the like, and it is spray drying in an embodiment.

Examples of an apparatus for spray drying include a spray dryer. The conditions for spray drying are not particularly limited, so long as the amorphous form of compound A or a pharmaceutically acceptable salt thereof, or the solid dispersion of compound A or a pharmaceutically acceptable salt thereof with the polymer can be obtained. For example, the inlet temperature is 90° C. to 150° C., and the product temperature is 50° C. to 70° C.

If the solvent remains after spray drying, for example, air drying, vacuum drying, drying under humid conditions, or the like, may be carried out for further drying.

In the melting method, compound A or a pharmaceutically acceptable salt thereof alone, or compound A or a pharmaceutically acceptable salt thereof and the polymer are heated and melted, and are then cooled.

The temperature during heating and melting can be appropriately set in accordance with the melting point of compound A or a pharmaceutically acceptable salt thereof, or the glass transition temperature of the polymer. The temperature is, for example, about 100° C. to about 250° C., and about 200° C. to about 250° C. in an embodiment.

An apparatus is not particularly limited, so long as compound A or a pharmaceutically acceptable salt thereof can be formed into the amorphous form, or the solid dispersion of compound A or a pharmaceutically acceptable salt thereof with the polymer can be obtained. Examples thereof include a twin-screw extruder.

In the mechanochemical method, compound A or a pharmaceutically acceptable salt thereof, or compound A or a pharmaceutically acceptable salt thereof and the polymer are pulverized and shocked. When rigid particles (such as granular crystalline cellulose) are further added, and the pulverization and shock are carried out, it sometimes becomes easy to be amorphized.

Examples of an apparatus include MECHANO FUSION AMS-MINI (HOSOKAWA MICRON CORPORATION), and the like.

Mixing Step

A mixing method is not particularly limited, so long as it is a conventional method in which each component can be pharmaceutically and uniformly mixed. Examples of an apparatus include a V-type mixer, a ribbon-type mixer, a container mixer, a high speed mixer, and the like.

Granulation Step

A granulation method is not particularly limited, so long as it is a conventional method in which granulation can be pharmaceutically carried out. Examples of an apparatus include a fluidized bed granulator, a melting agitation granulator, a high shear granulator, a milling (pulverization) and granulating machine, an extrusion granulator, a tumbling fluidized bed granulator, a spray granulator, a dry granulator, a twin-screw extruder, and the like. In an embodiment, it is a fluidized bed granulator or a high-speed agitation granulator, and in an embodiment, it is a fluidized bed granulator.

As an embodiment, an embodiment in which the polymer used in the present invention is added as a binder can be exemplified. A binder liquid may be prepared by dissolving or suspending a binder in a solvent, such as purified water, ethanol, methanol, or the like. Alternatively, a binder may be added to a granulator in a powder state, and granulation may be carried out while adding purified water, ethanol, methanol, or the like.

Examples of the binder include hypromellose, hydroxypropyl methylcellulose acetate succinate, polyvinyl pyrrolidone, hydroxypropyl cellulose, polyethylene glycol, copolyvidone, polyvinyl alcohol, methyl cellulose, ethyl cellulose, polyvinyl alcohol/polyethylene glycol graft copolymer, hydroxyethyl cellulose, methyl hydroxyethyl cellulose, carboxymethyl cellulose, carboxymethyl ethyl cellulose, hydroxypropyl methylcellulose phthalate, aminoalkyl methacrylate copolymer E, methacrylic acid copolymer L, dry methacrylic acid copolymer LD, methacrylic acid copolymer LD, methacrylic acid copolymer S, aminoalkyl methacrylate copolymer RS, and the like. In an embodiment, it is hypromellose, hydroxypropyl methylcellulose acetate succinate, polyethylene glycol, or the like; in an embodiment, it is hypromellose or polyethylene glycol; and in an embodiment, it is hypromellose.

The content of the binder is, for example, about 1% by weight to about 20% by weight, about 1% by weight to about 10% by weight in an embodiment, and about 1% by weight to about 5% by weight in an embodiment, with respect to the total weight of the pharmaceutical composition for oral administration.

Drying Step

A drying method is not particularly limited, so long as it is a conventional method in which drying can be pharmaceutically carried out. Examples of an apparatus include a forced-air dryer, a dryer under reduced pressure, a vacuum dryer, a fluid bed dryer, and the like.

After drying, the dried product may be sieved and sized using a sieve, a comil, or the like, if desired.

Forming (Tableting) Step

A forming method is not particularly limited, so long as it is a conventional method in which forming can be pharmaceutically carried out. Examples of an apparatus include a rotary tableting machine, a single punch tableting machine, an oil press, and the like.

In the forming step, for example, a method in which a granulated product containing the amorphous form of compound A or a pharmaceutically acceptable salt thereof, or a mixed product (a mixed product before compression-molding, in particular, a mixed product before tableting) prepared by mixing the granulated product with various pharmaceutical additives, such as a lubricant, is compression-molded to form tablets; a direct tableting method in which the drug (the amorphous form of compound A or a pharmaceutically acceptable salt thereof) is mixed with appropriate pharmaceutical additives, and the mixture is compression-molded to obtain tablets; or the like, may be used.

Film Coating Step

A film coating method is not particularly limited, so long as it is a conventional method in which film coating can be pharmaceutically carried out.

Examples of an apparatus include a pan coating machine, a fluidized bed coating machine, and the like.

As an embodiment, an embodiment in which the polymer used in the present invention is added as a base material for film coating can be exemplified. Examples of the base material for film coating include hypromellose, hydroxypropyl methylcellulose acetate succinate, polyvinyl pyrrolidone, hydroxypropyl cellulose, polyethylene glycol, copolyvidone, polyvinyl alcohol, methyl cellulose, ethyl cellulose, polyvinyl alcohol/polyethylene glycol graft copolymer, hydroxyethyl cellulose, methyl hydroxyethyl cellulose, carboxymethyl cellulose, carboxymethyl ethyl cellulose, hydroxypropyl methylcellulose phthalate, aminoalkyl methacrylate copolymer E, methacrylic acid copolymer L, dry methacrylic acid copolymer LD, methacrylic acid copolymer LD, methacrylic acid copolymer S, aminoalkyl methacrylate copolymer RS, and the like. In an embodiment, it is hypromellose, hydroxypropyl methylcellulose acetate succinate, polyethylene glycol, or the like; in an embodiment, it is hypromellose or polyethylene glycol; and in an embodiment, it is hypromellose.

The content of the base material for film coating is, for example, about 30% by weight to about 80% by weight, and about 50% by weight to about 75% by weight in an embodiment, with respect to the weight of the film coating layer. The content of the base material for film coating is, for example, about 0.01% by weight to about 10% by weight, about 0.01% by weight to about 5% by weight in an embodiment, about 0.1% by weight to about 5% by weight in an embodiment, and about 1% by weight to about 5% by weight in an embodiment.

Examples of a coloring agent Food Yellow No. 4, Food Yellow No. 5, Food Red No. 3, Food Red No. 102, Food Blue No. 3, ferric oxide (red, yellow), black iron oxide, titanium oxide, talc, and the like.

These base materials for film coating and coloring agents may be added alone, or as a combination of two or more, in appropriate amounts.

The film-coating rate is not particularly limited, so long as a film coating is formed on the pharmaceutical composition for oral administration. More particularly, it is about 0.01% by weight to about 10% by weight, about 0.01% by weight to about 5% by weight in an embodiment, about 0.1% by weight to about 5% by weight in an embodiment, and about 1% by weight to about 5% by weight in an embodiment.

If desired, after the film coating, the coated product may be dried. The coating method is not limited, so long as it is a conventional method in which drying can be pharmaceutically carried out. Examples of an apparatus include a pan coating machine, a fluidized bed coating machine, and the like. The conditions for drying are not particularly limited, so long as the conditions are appropriately determined depending on, for example, the stability of the formulation.

EXAMPLES

As compound A in the crystalline state used in the Examples below, a Y-type crystal that had been prepared in accordance with a method described in WO 2014/038663 was used.

The present invention will be further illustrated by, but is by no means limited to, the following Examples, Comparative Examples, and Experimental Examples.

Example 1

In a mixed solution (dichloromethane:methanol=6:4) of methanol (manufactured by KANTO CHEMICAL CO., INC.) and dichloromethane (manufactured by NIPPON RIKA CO. LTD), 40 g of compound A in the crystalline state and 40 g of hypromellose (TC-5E, manufactured by Shin-Etsu Chemical Co., Ltd., Unless otherwise stated, the same compound was used in the following Examples.) were dissolved, and the solution was spray-dried using a spray dryer (Spray Dryer DL41, manufactured by Yamato Scientific Co., Ltd.) to prepare a solid dispersion comprising compound A (the amorphous state) and a polymer (hypromellose).

Comparative Example 1

A suspension of Comparative Example 1 was obtained by suspending 100 mg of compound A in the crystalline state in 0.5% by weight of a methylcellulose solution.

<<Experimental Example 1>> Dissolution Test

A dissolution test was carried out by separately suspending 50 mg of compound A in the crystalline state and the solid dispersion of Example 1 (50 mg as the amount of compound A) in 0.5% by weight of a methylcellulose solution. The first fluid for dissolution test of the Japanese Pharmacopoeia (JP1) and the second fluid for dissolution test of the Japanese Pharmacopoeia (JP2) were used (volume of the test fluids: 500 mL, temperature of the fluids: 37° C.) as fluids for dissolution test, in accordance with Dissolution Test, method 2 (paddle method) described in the Japanese Pharmacopoeia, at a paddle rotation speed of 50 rpm. The results are shown in FIG. 1.

In both the first fluid for dissolution test of the Japanese Pharmacopoeia and the second fluid for dissolution test of the Japanese Pharmacopoeia, the dissolution rate of compound A from the solid dispersion of Example 1 was higher than that of compound A in the crystalline state, and it was found that the amorphization of compound A resulted in an improved dissolution rate.

<<Experimental Example 2>> Oral Absorption Test in Dog

A suspension prepared by suspending the solid dispersion (corresponding to 100 mg of compound A) obtained in Example 1 in 0.5% by weight of a methylcellulose solution, and the suspension of Comparative Example 1 were separately administered to dogs. After the administration, blood was periodically collected, and the concentration of compound A in plasma obtained by centrifugation was measured. The dogs were made to fast from the evening on the day before the administration (before more than 16 hours from the scheduled administration time) to the final blood collection on the day of the administration (24 hours after the administration). After the end of the final blood collection, food was given in accordance with the feeding amount of the breeding facility (the fasting period was from 24 hours or more to less than 48 hours). Water was not given during a time period from 30 minutes before the administration to 2 hours after the administration, and then, it was free to drink water.

The maximum drug concentration time (Tmax), the maximum drug concentration (Cmax), and the area under the blood concentration time curve from 0 to 24 hours ($AUC_{0-24hr}$) of the suspension of the solid dispersion of Example 1 and the suspension of Comparative Example 1 are shown in Table 1.

Compound A was hardly absorbed in the case of the suspension of Comparative Example 1, but the suspension of Example 1 exhibited high oral absorbability. Therefore, it was confirmed that the solid dispersion of compound A exhibits good oral absorbability.

TABLE 1

| | Comp. Ex. 1 | Ex. 1 |
| --- | --- | --- |
| Tmax (hr) | 4.0 ± 0.0 | 0.67 ± 0.29 |
| Cmax (ng/mL) | 29 ± 12 | 3300 ± 735 |
| $AUC_{0-24\ hr}$ (ng · hr/mL) | 341 ± 97 | 22315 ± 3141 |

Example 2

In 4137 g of methanol (manufactured by KANTO CHEMICAL CO., INC.) and 459.7 g of purified water, 70 g of compound A in the crystalline state was dissolved, and the solution was spray-dried using a spray dryer (TCSD, manufactured by NIPPON SHARYO, LTD., Unless otherwise stated, the same apparatus was used in the following Examples.) to prepare an amorphous form of compound A.

<<Experimental Example 3>> Measurement of Solubility

The solubility of compound A in the crystalline state and the amorphous form of compound A of Example 2 was measured (50 mg of compound A was added to 20 mL of each test solution, and shaken at room temperature for 120 minutes, and the solubility was measured.). The results are shown in Table 2. The improved solubility of compound A by amorphization was observed.

TABLE 2

|  | Compound A in crystalline state (mg/mL) | Ex. 2 (Compound A, amorphous form) (mg/mL) |
|---|---|---|
| Phosphate buffer, pH 6.8 | 0.015 | 0.075 |
| Phosphate buffer, pH 6.8 0.10% Sodium lauryl sulfate | 0.069 | 0.326 |

<<Experimental Example 4>> Measurement of Related Substances

The solid dispersion of Example 1 and the amorphous form of compound A of Example 2 were put into glass bottles, and the bottles were allowed to stand under the predetermined conditions, after being sealed or without being sealed, and the amount of each related substance of compound A was measured by an HPLC method.

The measurement of related substances was carried out in accordance with the following conditions (the following tests for related substances were carried out in a similar fashion.):

As a HPLC column, Unison UK-Phenyl (particle size=3 μm, 4.6 mm (inner diameter)×25 cm, manufactured by Imtakt), or its equivalent, was used, and maintained at 40° C.

As mobile phase A, a mixed solution (4:1) of a perchlorate solution (pH 4.0) and methanol was used.

As mobile phase B, acetonitrile was used.

Sample solutions were prepared by diluting samples with a mixed solution of mobile phase A/mobile phase B (7:3) so that the concentration of compound A became 250 μg/mL.

Related substances were measured using an ultraviolet absorption spectrophotometer (wavelength: 225 nm), in accordance with the gradient program shown in Table 3 below, and at a flow rate in which the retention time of compound A was about 26 minutes. The percentage of the peak area of each related substance was calculated, as a percentage with respect to the total peak area of compound A and its related substances.

TABLE 3

| Time from injection (min.) | Mobile phase A (%) | Mobile phase B (%) |
|---|---|---|
| 0-35 | 80 | 20 |
| 35-60 | 80 → 20 | 20 → 80 |
| 60-65 | 20 | 80 |
| 65-68 | 20 → 80 | 80 → 20 |
| 68-88 | 80 | 20 |

The results are shown in Table 4. In Table 4, the symbol "*" indicates the storage under the conditions where the bottle was not sealed. In Table 4, a numerical value in parentheses indicates an increased amount from the beginning of the storage. A significant increase in related substances was not observed in the solid dispersion containing compound A of Example 1, as well as the amorphous form of compound A of Example 2 (at least, 70° C. for 9 days, 40° C., 75% RH for 1 month, or 25° C., 60% RH for 1 month).

TABLE 4

|  |  | Ex. 1 | Ex. 2 |
|---|---|---|---|
| At the beginning of storage | Maximum related substance (%) | 0.81 | 0.80 |
|  | Total amount of related substances (%) | 1.00 | 0.88 |
| 70° C. for 9 days | Maximum related substance (%) | 0.82 (0.01) | 0.82 (0.02) |
|  | Total amount of related substances (%) | 1.05 (0.05) | 0.85 (−0.03) |
| 40° C., 75% RH for 1 month | Maximum related substance (%) | 0.79 (−0.02) | 0.79 (−0.01) |
|  | Total amount of related substances (%) | 1.56 (0.56) | 0.99 (0.11) |
| 40° C., 75% RH for 1 month * | Maximum related substance (%) | 0.76 (−0.05) | 0.77 (−0.03) |
|  | Total amount of related substances (%) | 1.64 (0.64) | 0.98 (0.10) |
| 25° C., 60% RH for 1 month | Maximum related substance (%) | 0.80 (−0.01) | 0.79 (−0.01) |
|  | Total amount of related substances (%) | 1.29 (0.29) | 0.99 (0.11) |

<<Experimental Example 5>> Powder X-Ray Diffraction Test

The amorphous form of compound A of Example 2 was put into glass bottles, and the bottles were sealed and allowed to stand under the predetermined conditions, and the crystallinity before and after storage was evaluated using a powder X-ray diffraction method. In "40° C., 75% RH for 1 month (opened)", the storage was carried out under the conditions where the bottle was not sealed. The results are shown in FIG. 2.

Figure 2:
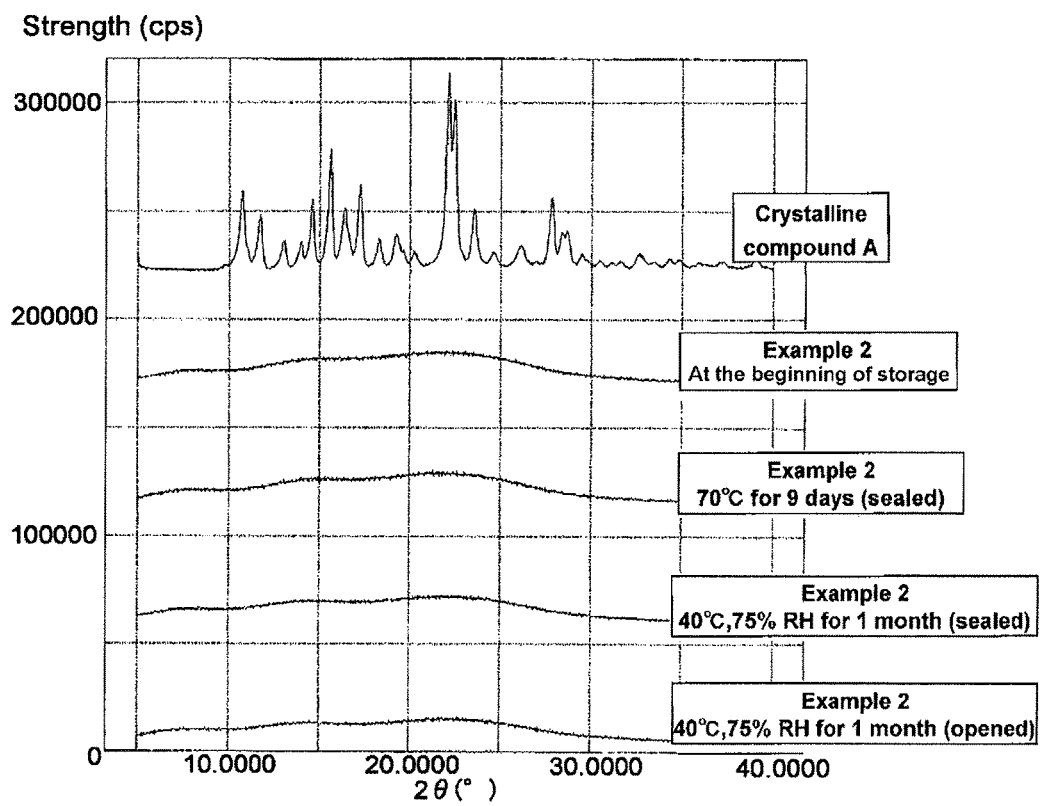
FIG. 2 is a graph showing the results of powder X-ray diffraction to evaluate the crystallinity of the amorphous form of compound A of Example 2 (and compound A in the crystalline state, as a control) before and after storage under various conditions.

As shown in FIG. 2, it was confirmed that the amorphous form of compound A of Example 2 maintained the amorphous state alone, even after storage under various conditions (at least, 70° C. for 9 days, or 40° C., 75% RH for 1 month).

It was confirmed that the amorphous form of compound A is stable, in the state of the amorphous form alone.

<<Experimental Example 6>> Oral Absorption Test in Dog

A suspension prepared by suspending the solid dispersion (corresponding to 50 mg of compound A) obtained in Example 1 in 0.5% by weight of a methylcellulose solution, and a suspension prepared by suspending the amorphous form of compound A (corresponding to 50 mg of compound A) obtained in Example 2 in 0.5% by weight of a methylcellulose solution were separately administered to dogs. The administration test to dogs was carried out in the same manner as that of Experimental Example 2. After the administration, blood was periodically collected, and the concentration of compound A in plasma obtained by centrifugation was measured.

The Cmax and the $AUC_{0-24hr}$ of the suspension of the solid dispersion of Example 1 and the suspension of the amorphous form of compound A of Example 2 are shown in Table 5.

Further, the Cmax ratio and the $AUC_{0-24hr}$ ratio of the suspension of Example 1 to the suspension of Example 2 are shown in Table 6.

It was confirmed that the oral absorbability of the solid dispersion of compound A (Example 1) was the same as that of the amorphous form of compound A (Example 2), and the amorphous form of compound A exhibited good oral absorbability.

Therefore, it was confirmed that the amorphous form of compound A (Example 2) alone exhibits good stability and good oral absorbability, without the co-existence of a polymer used as a stabilizer for an amorphous form.

TABLE 5

|  | Ex. 1 | Ex. 2 |
|---|---|---|
| Cmax (ng/mL) | 916 ± 235 | 793 ± 165 |
| $AUC_{0-24\ hr}$ (ng · hr/mL) | 5883 ± 1915 | 4925 ± 1219 |

TABLE 6

|  | Cmax | $AUC_{0-24\ h}$ |
|---|---|---|
| Ex. 1 | 1.16 | 1.19 |
| Ex. 2 | 1.00 | 1.00 |

Example 3

In 39.4 kg of methanol/water (9:1), 600 g of compound A in the crystalline state was dissolved, and the solution was spray-dried using a spray dryer to prepare 433.7 g of an amorphous form of compound A. In accordance with the formulation shown in Table 7, 2.088 g of the amorphous form of compound A was mixed with 653.2 g of D-mannitol (Pearitol 50C, manufactured by Roquette, Unless otherwise stated, the same compound was used in the following Examples.) using a fluidized bed granulator (FLO-01, manufactured by Freund Corporation). After the mixing, the mixture was granulated by spraying a hypromellose aqueous solution (solid content: 10% by weight) as a binder, and dried to obtain a granulated product.

The granulation was repeated one more time, and 1269.0 g of the obtained granulated product was sieved, and mixed with 67.5 g of croscarmellose sodium (Ac-Di-Sol, manufactured by FMC, Unless otherwise stated, the same compound was used in the following Examples.) and 13.5 g of magnesium stearate (Parteck (registered trademark) LUB MST, manufactured by MERCK, Unless otherwise stated, the same compound was used in the following Examples.) using a mixer (DC mixer, manufactured by Suzuman) to obtain a mixed product before tableting.

The obtained mixed product was formed into tablets, using a rotary tableting machine (HT-X20, manufactured by HATA TEKKOSHO Co., Ltd.), to obtain tablets (uncoated tablets).

A film-coating machine (HCT-30, manufactured by Freund Corporation) was used to film-coat 1000 g of the obtained uncoated tablets with a liquid, in which pharmaceutical additives were dispersed in accordance with the formulation shown in Table 8, to obtain tablets (film-coated tablets).

TABLE 7

| (Unit: mg) | Ex. 3 | Ex. 4 | Ex. 5 |
|---|---|---|---|
| Compound A, amorphous form | 0.5 | 5 | 50 |
| D-mannitol | 163.3 | 158.8 | 113.8 |
| Hypromellose | 5.4 | 5.4 | 5.4 |
| Croscarmellose sodium | 9 | 9 | 9 |
| Magnesium stearate | 1.8 | 1.8 | 1.8 |
| Weight of uncoated tablet | 180 | 180 | 180 |
| Film coating agent | 9 | 9 | 9 |
| Weight of tablet | 189 | 189 | 189 |

TABLE 8

|  | Content (%) |
|---|---|
| Hypromellose | 60.610 |
| Titanium oxide | 7.580 |
| Polyethylene glycol 8000 | 11.360 |
| Talc | 18.180 |
| Yellow ferric oxide | 2.270 |

Examples 4 and 5

In accordance with the formulations shown in Table 7, tablets of Examples 4 and 5 (film-coated tablets) were obtain in the same manner as that of Example 3.

<<Experimental Example 7>> Disintegration Test

With respect to the tablets (film-coated tablets) of Examples 3 to 5, a disintegration test was carried out using purified water in accordance with Disintegration Test described in the Japanese Pharmacopoeia. Six tablets for each were used in the disintegration test, and the average of the disintegration time was calculated. The results are shown in Table 9.

Example 5 containing the amorphous form of compound A at a high content also exhibited rapid disintegration properties.

TABLE 9

|  | Ex. 3 | Ex. 4 | Ex. 5 |
|---|---|---|---|
| Disintegration time (min.) | 4.5 | 4.0 | 5.4 |

<<Experimental Example 8>> Measurement of Related Substances, Measurement of Dissolution Rate, and Powder X-Ray Diffraction The tablets (film-coated tablets) of Examples 3 to 5 were packaged using aluminum/aluminum blister, and were allowed to stand at 40° C., 75% RH. The related substances, the dissolution rate, and the crystalline state of compound A (crystalline form or amorphous form) were evaluated.

In the related substance test, the measurement was carried out by an HPLC method.

In the dissolution test, with respect to the tablets of Examples 3 and 4, a phosphate buffer, pH 6.8 (volume of the test fluid: 900 mL, temperature of the fluid: 37° C.) was used as a fluid for dissolution test, in accordance with Dissolution Test, method 2 (paddle method) described in the Japanese Pharmacopoeia, at a paddle rotation speed of 50 rpm, and with respect to the tablet of Example 5, a phosphate buffer, pH 6.8 supplemented with 0.10% of sodium lauryl sulfate (volume of the test fluid: 900 mL, temperature of the fluid: 37° C.) was used as a fluid for dissolution test, in accordance with Dissolution Test, method 2 (paddle method) described in the Japanese Pharmacopoeia, at a paddle rotation speed of 50 rpm.

In the evaluation of the crystalline state of compound A, the measurement was carried out by a powder X-ray diffraction method.

The results are shown in Tables 10 to 12. In Tables 10 to 12, a numerical value in parentheses indicates an increased amount from the beginning of the storage. During the storage, an increase in related substances, a decrease in dissolution rate, and the crystallization of compound A were not observed, and the tablets exhibited good stability.

TABLE 10

Example 3, storage conditions: 40° C., 75% RH

| | | At the beginning of storage | 1 month | 3 months | 6 months |
|---|---|---|---|---|---|
| Related Substances (%) | Maximum related substance | 0.73 | 0.73 (0.00) | 0.72 (−0.01) | 0.72 (−0.01) |
| | Total amount of related substances | 2.80 | 2.85 (0.05) | 2.79 (−0.01) | 2.75 (−0.05) |
| Dissolution rate (%) | Value in 15 min. | 97 | 97 | 94 | 97 |
| | Value in 30 min. | 99 | 98 | 98 | 100 |
| Crystalline/amorphous of compound A | | Amorphous | Amorphous | Amorphous | Amorphous |

TABLE 11

Example 4, storage conditions: 40° C., 75% RH

| | | At the beginning of storage | 1 month | 3 months | 6 months |
|---|---|---|---|---|---|
| Related Substances (%) | Maximum related substance | 0.73 | 0.72 (−0.01) | 0.73 (0.00) | 0.73 (0.00) |
| | Total amount of related substances | 2.71 | 2.80 (0.09) | 2.73 (0.02) | 2.74 (0.03) |
| Dissolution rate (%) | Value in 15 min. | 89 | 88 | 87 | 88 |
| | Value in 30 min. | 98 | 97 | 97 | 98 |
| Crystalline/amorphous of compound A | | Amorphous | Amorphous | Amorphous | Amorphous |

TABLE 12

Example 5, storage conditions: 40° C., 75% RH

| | | At the beginning of storage | 1 month | 3 months | 6 months |
|---|---|---|---|---|---|
| Related Substances (%) | Maximum related substance | 0.73 | 0.73 (0.00) | 0.72 (−0.01) | 0.72 (−0.01) |
| | Total amount of related substances | 2.71 | 2.78 (0.07) | 2.68 (−0.03) | 2.68 (−0.03) |
| Dissolution rate (%) | Value in 15 min. | 86 | 85 | 86 | 79 |
| | Value in 30 min. | 93 | 93 | 94 | 90 |
| Crystalline/amorphous of compound A | | Amorphous | Amorphous | Amorphous | Amorphous |

Example 6

In 72 kg of acetone/water (9:1), 8.0 kg of compound A in the crystalline state was dissolved, and the solution was spray-dried using a spray dryer. The spray drying was repeated two more times to obtain 23.593 kg of an amorphous form of compound A.

In accordance with the formulation shown in Table 13, 81.47 g of the amorphous form of compound A was mixed with 12940 g of D-mannitol using a fluidized bed granulator (GPCG15/30, manufactured by Powrex Corporation). After the mixing, the mixture was granulated by spraying a hypromellose aqueous solution (solid content: 10% by weight) as a binder, and dried to obtain a granulated product.

The granulation was repeated one more time, and 26012 g of the obtained granulated product was sieved, and mixed with 1384 g of croscarmellose sodium and 276.7 g of magnesium stearate using a mixer (container mixer PM200, manufactured by Kotobuki Engineering & Manufacturing Co., Ltd.) to obtain a mixed product before tableting.

The obtained mixed product before tableting was formed into tablets, using a rotary tableting machine (HT-X20, manufactured by HATA TEKKOSHO Co., Ltd.), to obtain tablets (uncoated tablets).

A film-coating machine (aqua coater 60/80, manufactured by Freund Corporation) was used to film-coat 23271 g of the obtained uncoated tablets with a liquid, in which pharmaceutical additives were dispersed in accordance with the formulation shown in Table 8, to obtain tablets (film-coated tablets).

TABLE 13

| (Unit: mg) | Ex. 6 | Ex. 7 | Ex. 8 |
|---|---|---|---|
| Compound A, amorphous form | 1 | 10 | 100 |
| D-mannitol | 162.8 | 153.8 | 227.6 |
| Hypromellose | 5.4 | 5.4 | 10.8 |
| Croscarmellose sodium | 9 | 9 | 18 |
| Magnesium stearate | 1.8 | 1.8 | 3.6 |
| Weight of uncoated tablet | 180 | 180 | 360 |
| Film coating agent | 9 | 9 | 10.8 |
| Weight of tablet | 189 | 189 | 370.8 |

Examples 7 and 8

In accordance with the formulations shown in Table 13, tablets of Examples 7 and 8 (film-coated tablets) were obtained in the same manner as that of Example 6.

<<Experimental Example 9>> Measurement of Related Substances and Measurement of Dissolution Rate The tablets (film-coated tablets) of Examples 6 to 8 were packaged using aluminum/aluminum blisters, and were allowed to stand at 40° C., 75% RH. The related substances and the dissolution rate were measured.

In the related substance test, the measurement was carried out by an HPLC method.

In the dissolution test, with respect to the tablets of Examples 6 and 7, a phosphate buffer, pH 6.8 (volume of the test fluid: 900 mL, temperature of the fluid: 37° C.) was used as a fluid for dissolution test, in accordance with Dissolution Test, method 2 (paddle method) described in the Japanese Pharmacopoeia, at a paddle rotation speed of 50 rpm, and with respect to the tablet of Example 8, a phosphate buffer, pH 6.8 supplemented with 0.10% of hexadecyltrimethylammonium bromide (volume of the test fluid: 900 mL, temperature of the fluid: 37° C.) was used as a fluid for dissolution test, in accordance with Dissolution Test, method 2 (paddle method) described in the Japanese Pharmacopoeia, at a paddle rotation speed of 75 rpm.

The results are shown in Tables 14 to 16. In Tables 14 to 16, a numerical value in parentheses indicates an increased amount from the beginning of the storage. During the storage, an increase in related substances and a decrease in dissolution rate were not observed, and the tablets exhibited good stability.

TABLE 14

Example 6, storage conditions: 40° C., 75% RH

|  |  | At the beginning of storage | 1 month | 3 months | 6 months |
|---|---|---|---|---|---|
| Related Substances (%) | Maximum related substance | 0.75 | 0.75 (0.00) | 0.76 (0.01) | 0.76 (0.01) |
|  | Total amount of related substances | 1.06 | 1.05 (−0.01) | 1.06 (0.00) | 1.06 (0.00) |
| Dissolution rate (%) | Value in 15 min. | 72 | 73 | 71 | 70 |
|  | Value in 30 min. | 88 | 89 | 87 | 87 |

TABLE 15

Example 7, storage conditions: 40° C., 75% RH

|  |  | At the beginning of storage | 1 month | 3 months | 6 months |
|---|---|---|---|---|---|
| Related Substances (%) | Maximum related substance | 0.77 | 0.76 (−0.01) | 0.77 (0.00) | 0.76 (−0.01) |
|  | Total amount of related substances | 1.08 | 1.07 (−0.01) | 1.07 (−0.01) | 1.06 (−0.02) |
| Dissolution rate (%) | Value in 15 min. | 60 | 59 | 58 | 60 |
|  | Value in 30 min. | 81 | 81 | 80 | 81 |

TABLE 16

Example 8, storage conditions: 40° C., 75% RH

|  |  | At the beginning of storage | 1 month | 3 months | 6 months |
|---|---|---|---|---|---|
| Related Substances (%) | Maximum related substance | 0.76 | 0.75 (−0.01) | 0.75 (−0.01) | 0.75 (−0.01) |
|  | Total amount of related substances | 1.06 | 1.05 (−0.01) | 1.05 (−0.01) | 1.04 (−0.02) |
| Dissolution rate (%) | Value in 15 min. | 90 | 93 | 91 | 87 |
|  | Value in 30 min. | 95 | 96 | 95 | 93 |

Examples 9 to 14

The amorphous form of compound A, obtained in the same manner as that of Example 2, was mixed with hypromellose or hydroxypropyl methylcellulose acetate succinate (AQOAT (registered trademark) MG grade, manufactured by Shin-Etsu Chemical Co., Ltd., hereinafter also referred to as HPMC-AS) in accordance with the formulations shown in Table 17 to obtain mixed products.

TABLE 17

| (Unit: mg) | Ex. 9 | Ex. 10 | Ex. 11 | Ex. 12 | Ex. 13 | Ex. 14 |
|---|---|---|---|---|---|---|
| Compound A, amorphous form | 100 | 100 | 100 | 100 | 100 | 100 |
| Hypromellose | 2.7 | 5.4 | 10.8 | — | — | — |
| HPMC-AS | — | — | — | 2.7 | 5.4 | 10.8 |

<<Experimental Example 10>> Dissolution Test

Figure 3:
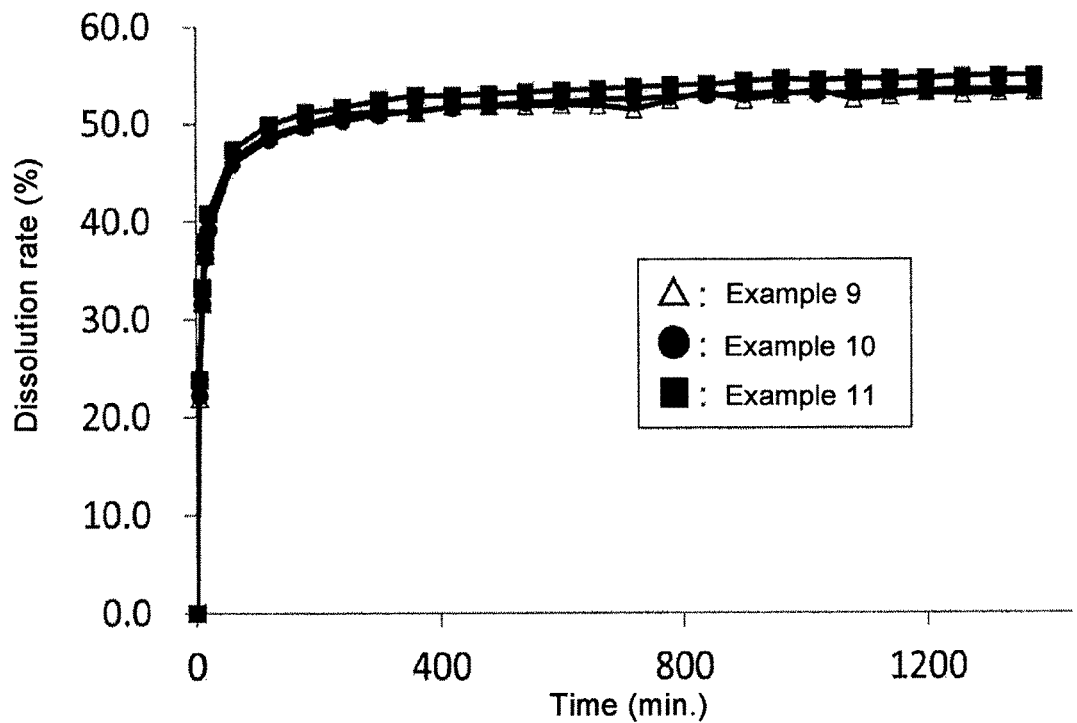
FIG. 3 is a graph showing the results of a dissolution test for the pharmaceutical compositions of Examples 9 to 11.
Figure 4:
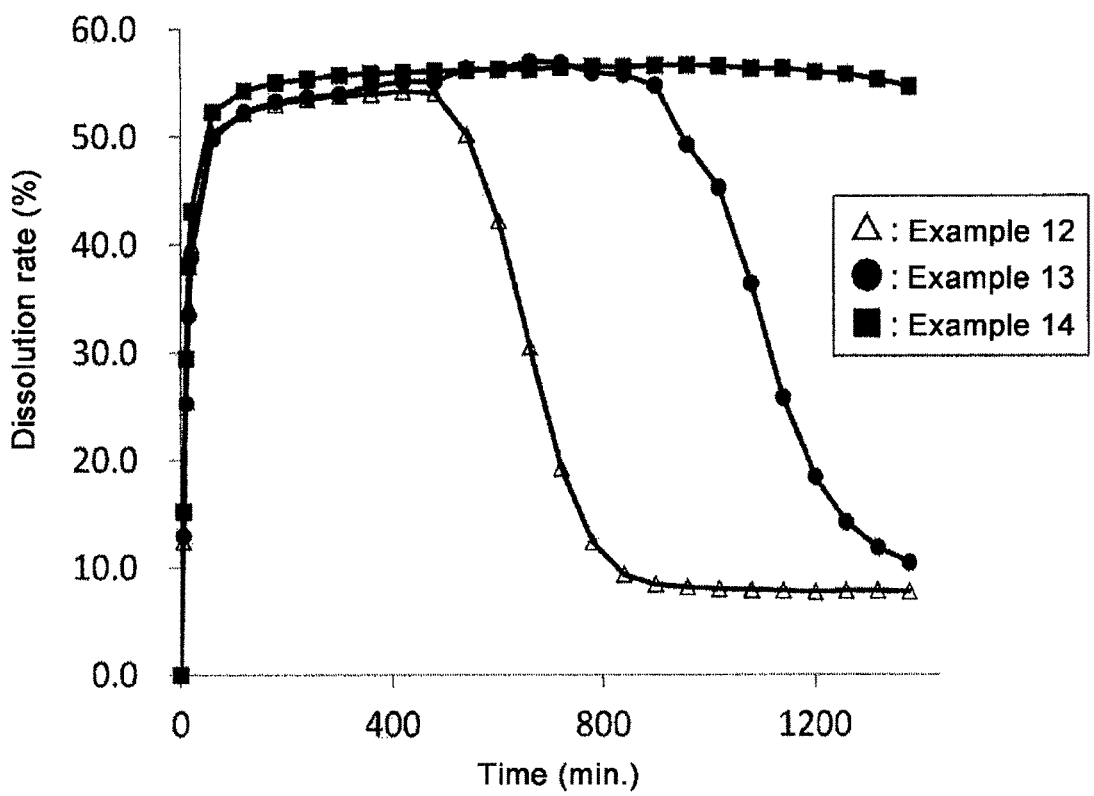
FIG. 4 is a graph showing the results of a dissolution test for the pharmaceutical compositions of Examples 12 to 14.

A dissolution test for the pharmaceutical compositions obtained in Examples 9 to 14 was carried out using a USP (U.S. Pharmacopeia) buffer, pH 4.5 (volume of the test fluid: 500 mL, temperature of the fluid: 37° C.) as a fluid for dissolution test, in accordance with Dissolution Test, method 2 (paddle method) described in the Japanese Pharmacopoeia, at a paddle rotation speed of 200 rpm. The results are shown in FIGS. 3 and 4.

It was confirmed that hypromellose as well as HPMC-AS could maintain a supersaturated state, and hypromellose maintained the supersaturated state for a longer period of time.

Examples 15 to 18

In accordance with the formulations shown in Table 18, amorphous forms of compound A obtained in the same manner of that of Example 6 were used to obtain tablets (uncoated tablets) in a 200-tablet scale, in accordance with the same production method as that of Example 3. Kiccolate ND-2HS (manufactured by Asahi Kasei Chemicals Corporation) as croscarmellose sodium, Kollidon CL (manufactured by BASF) as crospovidone, Primojel (manufactured by DFE pharma) as sodium starch glycolate, and L-HPC LH21 (manufactured by Shin-Etsu Chemical Co., Ltd.) as low-substituted hydroxypropyl cellulose, were respectively used.

TABLE 18

| (Unit: mg) | Ex. 15 | Ex. 16 | Ex. 17 | Ex. 18 |
|---|---|---|---|---|
| Compound A, amorphous form | 100 | 100 | 100 | 100 |
| D-mannitol | 227.6 | 227.6 | 227.6 | 227.6 |
| Hypromellose | 10.8 | 10.8 | 10.8 | 10.8 |
| Croscarmellose sodium | 18 | — | — | — |
| Crospovidone | — | 18 | — | — |
| Sodium starch glycolate | — | — | 18 | — |
| Low-substituted hydroxypropyl cellulose | — | — | — | 18 |
| Magnesium stearate | 3.6 | 3.6 | 3.6 | 3.6 |
| Total weight (mg) | 360 | 360 | 360 | 360 |

<<Experimental Example 11>> Dissolution Test

Figure 5:
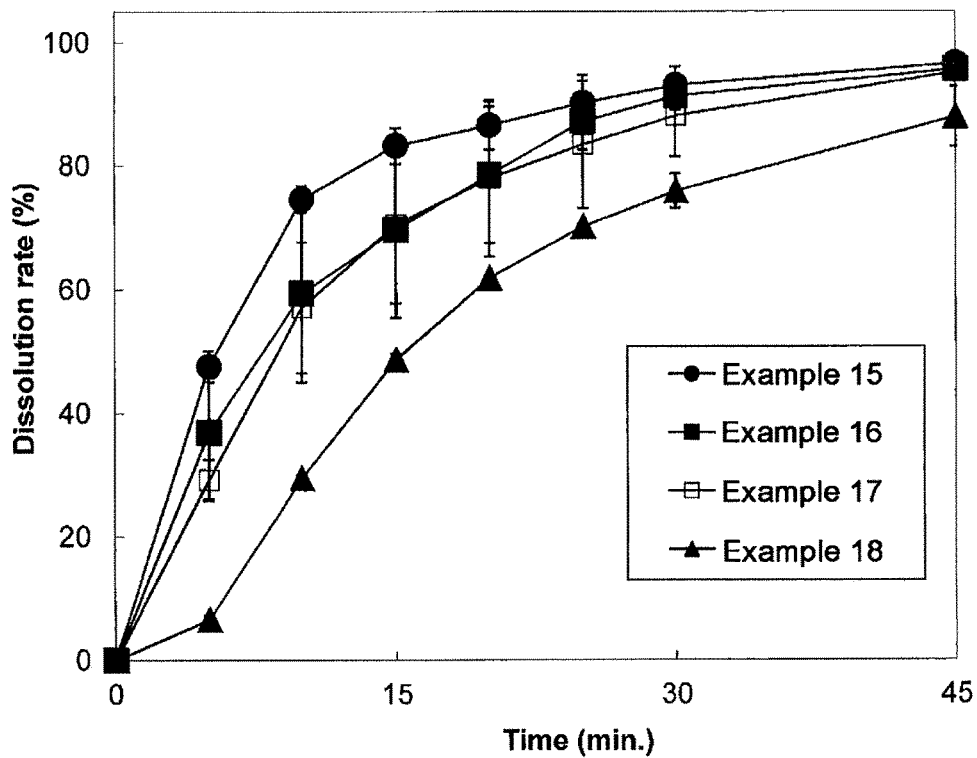
FIG. 5 is a graph showing the results of a dissolution test for the tablets (uncoated tablets) of Examples 15 to 18.

A dissolution test for the tablets obtained in Examples 15 to 18 was carried out using a phosphate buffer, pH 6.8 supplemented with 0.1% by weight of sodium lauryl sulfate (volume of the test fluid: 900 mL, temperature of the fluid: 37° C.) as a fluid for dissolution test, in accordance with Dissolution Test, method 2 (paddle method) described in the Japanese Pharmacopoeia, at a paddle rotation speed of 50 rpm. The results are shown in FIG. 5.

All the Examples exhibited rapid dissolution properties, and in particular, croscarmellose sodium exhibited the most rapid dissolution properties.

Examples 19 to 22

In accordance with the formulations shown in Table 19, tablets (uncoated tablets) of Examples 19 to 22 were obtained in accordance with the same production method as that of Example 3. With respect to Examples 19 and 20, tablets (film-coated tablets) were obtained in accordance with the same production method as that of Example 3, using a liquid, in which pharmaceutical additives were dispersed in accordance with the formulation shown in Table 8.

TABLE 19

| (Unit: mg) | Ex. 19 | Ex. 20 | Ex. 21 | Ex. 22 |
|---|---|---|---|---|
| Compound A, amorphous form | 0.5 | 0.5 | 50 | 50 |
| D-mannitol | 171.5 | 171.5 | 122 | 122 |
| Hypromellose | 6 | 6 | 6 | 6 |
| Croscarmellose sodium | 10 | — | 10 | — |
| Low-substituted hydroxypropyl cellulose | — | 20 | — | 20 |
| Magnesium stearate | 1.9 | 2 | 1.9 | 2 |
| Film coating agent | 5.7 | 6 | — | — |
| Total weight (mg) | 195.6 | 206 | 189.9 | 200 |

<<Experimental Example 12>> Measurement of Related Substances and Measurement of Dissolution Rate The tablets (film-coated tablets) of Examples 19 and 20 were packaged using aluminum/aluminum blisters, and were allowed to stand at 70° for 9 days or at 40° C., 75% RH for a month. The related substances were measured.

The related substances were measured by a HPLC method.

A dissolution test for the tablets of Examples 21 and 22 was carried out using a 1/10-diluted USP (U.S. Pharmacopeia) phosphate buffer, pH 6.8 supplemented with 0.1% by weight of sodium lauryl sulfate (volume of the test fluid: 900 mL, temperature of the fluid: 37° C.) as a fluid for dissolution test, in accordance with Dissolution Test, method 2 (paddle method) described in the Japanese Pharmacopoeia, at a paddle rotation speed of 50 rpm.

Figure 6:
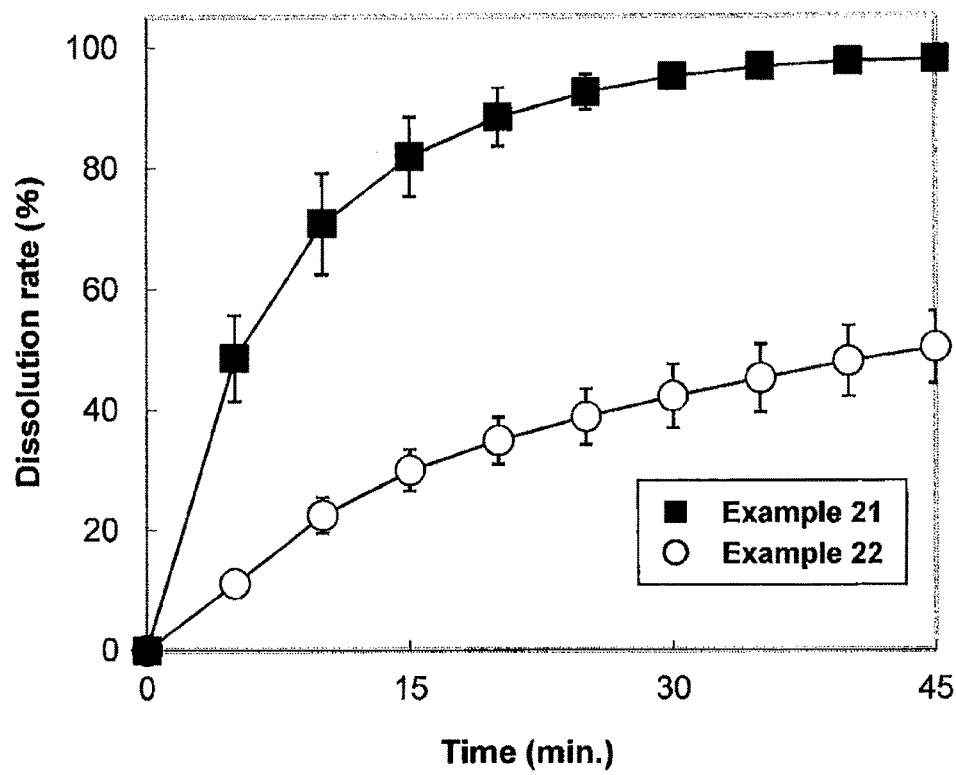
FIG. 6 is a graph showing the results of a dissolution test for the tablets (uncoated tablets) of Examples 21 to 22.

The results are shown in Table 20, Table 21, and FIG. 6. In Tables 20 and 21, a numerical value in parentheses indicates an increased amount from the beginning of the storage. Croscarmellose sodium exhibited more stable and more rapid dissolution properties.

TABLE 20

| | | Example 19 | | |
|---|---|---|---|---|
| | | At the beginning of storage | 70° C. for 9 days | 40° C., 75% RH for 1 month |
| Related substances (%) | Maximum related substance | 0.79 | 0.62 (−0.17) | 0.78 (−0.01) |
| | Total amount of related substances | 0.93 | 1.17 (0.24) | 0.87 (−0.06) |

TABLE 21

| | | Example 20 | | |
|---|---|---|---|---|
| | | At the beginning of storage | 70° C. for 9 days | 40° C., 75% RH for 1 month |
| Related substances (%) | Maximum related substance | 0.79 | 0.64 (−0.15) | 0.79 (0.00) |
| | Total amount of related substances | 1.11 | 1.44 (0.33) | 1.79 (0.68) |

INDUSTRIAL APPLICABILITY

According to the present invention, a pharmaceutical composition enabling improved solubility, improved dissolution properties, and improved oral absorbability of compound A or a pharmaceutically acceptable salt thereof, as well as size reduction, can be provided.

Although the present invention has been described with reference to specific embodiments, various changes and modifications obvious to those skilled in the art are possible without departing from the scope of the appended claims.

The invention claimed is:

1. A pharmaceutical composition for oral administration, comprising an amorphous form of (2R)—N-({5-[3-(2,5-difluorophenyl)-2-(1,3-dihydro-2H-benzimidazole-2-ylidene)-3-oxopropanoyl]-2-fluorophenyl}sulfonyl)-2-hydroxypropane imide amide or a pharmaceutically acceptable salt thereof, and a polymer.

2. The pharmaceutical composition for oral administration according to claim 1, wherein the polymer is a polymer or two or more polymers selected from the group consisting of hypromellose, hydroxypropyl methylcellulose acetate succinate, polyvinyl pyrrolidone, hydroxypropyl cellulose, polyethylene glycol, copolyvidone, and polyvinyl alcohol.

3. The pharmaceutical composition for oral administration according to claim 1, wherein the mixing ratio of the polymer is about 10% by weight to about 500% by weight with respect to the weight of the amorphous form of (2R)—N-({5-[3-(2,5-difluorophenyl)-2-(1,3-dihydro-2H-benzimidazole-2-ylidene)-3-oxopropanoyl]-2-fluorophenyl}sulfonyl)-2-hydroxypropane imide amide or a pharmaceutically acceptable salt thereof.

4. The pharmaceutical composition for oral administration according to claim 1, wherein the mixing ratio of the polymer is about 0.01% by weight to about 30% by weight with respect to the total weight of the pharmaceutical composition for oral administration.

5. The pharmaceutical composition for oral administration according to claim 1, wherein the polymer is hypromellose and/or polyethylene glycol.

6. The pharmaceutical composition for oral administration according to claim 1, wherein the polymer is hypromellose.

7. The pharmaceutical composition for oral administration according to claim 1, wherein the polymer is contained as a binder and/or a base material for film coating.

8. The pharmaceutical composition for oral administration according to claim 1, wherein the pharmaceutical composition for oral administration is a tablet.

9. The pharmaceutical composition for oral administration according to claim 1, further comprising a disintegrating agent.

10. The pharmaceutical composition for oral administration according to claim 9, wherein the disintegrating agent is croscarmellose sodium.

11. The pharmaceutical composition for oral administration according to claim 9, wherein the mixing ratio of the disintegrating agent is about 0.1% by weight to about 30% by weight with respect to the total weight of the pharmaceutical composition.

12. A stable pharmaceutical composition for oral administration, comprising an amorphous form of (2R)—N-({5-[3-(2,5-difluorophenyl)-2-(1,3-dihydro-2H-benzimidazole-2-ylidene)-3-oxopropanoyl]-2-fluorophenyl}sulfonyl)-2-hydroxypropane imide amide or a pharmaceutically acceptable salt thereof.

13. The pharmaceutical composition for oral administration according to claim 12, further comprising a pharmaceutical additive.

14. A process of manufacturing a pharmaceutical composition for oral administration comprising an amorphous form of (2R)—N-({5-[3-(2,5-difluorophenyl)-2-(1,3-dihydro-2H-benzimidazole-2-ylidene)-3-oxopropanoyl]-2-fluorophenyl}sulfonyl)-2-hydroxypropane imide amide or a pharmaceutically acceptable salt thereof, and a polymer.

15. A pharmaceutical composition for oral administration, comprising an amorphous form of (2R)—N-({5-[3-(2,5-difluorophenyl)-2-(1,3-dihydro-2H-benzimidazole-2-ylidene)-3-oxopropanoyl]-2-fluorophenyl}sulfonyl)-2-hydroxypropane imide amide and hypromellose.

16. The pharmaceutical composition of claim 15, further comprising a disintegrating agent.

17. The pharmaceutical composition of claim 16, wherein the disintegrating agent is croscarmellose sodium.

* * * * *